United States Patent
Xie et al.

(10) Patent No.: US 11,421,379 B2
(45) Date of Patent: Aug. 23, 2022

(54) ENZYMATIC TREATMENT OF CELLULOSIC TEXTILE

(71) Applicant: Novozymes A/S, Bagsvaerd (DK)

(72) Inventors: Shuang Xie, Beijing (CN); Lijuan Cao, Beijing (CN); Yucheng Zhou, Beijing (CN)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 15/309,850

(22) PCT Filed: May 15, 2015

(86) PCT No.: PCT/CN2015/079095
§ 371 (c)(1),
(2) Date: Nov. 9, 2016

(87) PCT Pub. No.: WO2015/172742
PCT Pub. Date: Nov. 19, 2015

(65) Prior Publication Data
US 2017/0145628 A1 May 25, 2017

(30) Foreign Application Priority Data
May 15, 2014 (WO) ............... PCT/CN2014/077573

(51) Int. Cl.
*D06M 16/00* (2006.01)
*C08L 71/02* (2006.01)
*C12N 9/24* (2006.01)
*C12N 9/88* (2006.01)
*D06B 3/20* (2006.01)

(52) U.S. Cl.
CPC ........... *D06M 16/003* (2013.01); *C08L 71/02* (2013.01); *C12N 9/2402* (2013.01); *C12N 9/88* (2013.01); *C12Y 302/01015* (2013.01); *C12Y 402/0201* (2013.01); *D06B 3/201* (2013.01); *C08L 2205/025* (2013.01); *D06B 2700/09* (2013.01)

(58) Field of Classification Search
CPC ......... D06M 16/003; C12Y 302/01015; C12Y 402/024; C12Y 402/0201; C08L 71/02; C08L 2205/025; D06B 3/201; D06B 2700/09; C12N 9/2402; C12N 9/88
See application file for complete search history.

(56) References Cited

U.S. PATENT DOCUMENTS

| | | | | |
|---|---|---|---|---|
| 6,607,902 B2 * | 8/2003 | Schroder et al. | .. | C11D 3/38636 435/232 |
| 2002/0142438 A1 | 10/2002 | Andersen | | |
| 2002/0165115 A1 * | 11/2002 | Daniels | ............ | C07C 43/11 510/421 |
| 2003/0089381 A1 * | 5/2003 | Manning, Jr. | ......... | C11D 3/0047 134/1 |
| 2003/0175940 A1 | 9/2003 | Schroder Glad et al. | | |
| 2007/0192981 A1 * | 8/2007 | Lawshe | ............ | A47K 5/06 15/222 |
| 2009/0227975 A1 | 10/2009 | Dougherty, Jr. et al. | | |
| 2012/0036649 A1 * | 2/2012 | Auterinen | ................. | D06L 4/40 8/111 |
| 2012/0231991 A1 * | 9/2012 | Mukherjee | ........... | C11D 3/0036 510/476 |
| 2014/0066583 A1 | 3/2014 | Yoneda | | |

FOREIGN PATENT DOCUMENTS

| | | | | |
|---|---|---|---|---|
| CN | 1912224 | | 2/2007 | |
| CN | 1912224 A | | 2/2007 | |
| CN | 1986953 | | 6/2007 | |
| CN | 1986953 A | | 6/2007 | |
| CN | 101736598 | * | 6/2010 | |
| CN | 101736598 A | | 6/2010 | |
| CN | 101929064 A | | 12/2010 | |
| CN | 102154840 | | 8/2011 | |
| CN | 102191692 | | 9/2011 | |
| CN | 102191692 a | | 9/2011 | |
| CN | 102559421 | | 7/2012 | |
| CN | 102559421 A | | 7/2012 | |
| CN | 103046383 | * | 4/2013 | ............... D06L 3/02 |
| EP | 0943028 B1 | | 11/1997 | |
| EP | 1159479 B1 | | 10/1999 | |
| EP | 1159479 B1 | | 6/2007 | |
| EP | 0943028 B1 | | 8/2007 | |
| WO | 9701629 A1 | | 1/1997 | |
| WO | 2006002034 A1 | | 1/2006 | |
| WO | 2007136469 A2 | | 11/2007 | |
| WO | 2008039353 A2 | | 4/2008 | |
| WO | 2009/021813 A2 | | 2/2009 | |
| WO | 2009021813 A2 | | 2/2009 | |
| WO | 2012089024 A1 | | 7/2012 | |

OTHER PUBLICATIONS

Dong et al., Chemistry and Application of Textile Auxiliary Agent, pp. 334-335 (2007).
Wang, 2009, China Textile Press, 604.

* cited by examiner

*Primary Examiner* — Amina S Khan
(74) *Attorney, Agent, or Firm* — Elias Lambiris

(57) ABSTRACT

A process for treatment of cellulosic material, for example, knitted or woven cotton fabric or yarn, comprises treating cellulosic material with a pectinase and a surfactant.

14 Claims, No Drawings
Specification includes a Sequence Listing.

ENZYMATIC TREATMENT OF CELLULOSIC TEXTILE

CROSS-REFERENCE TO RELATED APPLICATIONS

This application is a 35 U.S.C. 371 national application of international application no. PCT/CN2015/079095 filed May 15, 2015, which claims priority or the benefit under 35 U.S.C. 119 of international application no. PCT/CN2014/077573 filed May 15, 2014. The content of these applications is fully incorporated herein by reference.

REFERENCE TO A SEQUENCE LISTING

This application contains a Sequence Listing in computer readable form, which is incorporated herein by reference.

FIELD OF THE INVENTION

The present invention relates to methods for biopreparation of cellulosic material, particularly textiles and most particularly cotton textile, using pectinase in combination with surfactants.

BACKGROUND OF THE INVENTION

An important aspect of the preparation of textiles from cellulosic fibers is the removal of non-cellulosic components found in the native fiber, as well as the removal of impurities, such as compounds added to the fiber as sizing and lubricants used in the processing machinery. The removal of non-cellulosic impurities, termed "scouring", optimally results in a fabric with a high and even wettability that, consequently, can be evenly bleached and/or dyed.

Conventional scouring processes typically utilize highly alkaline chemical treatment, which results not only in removal of impurities but also in weakening of the underlying cellulose component of the fiber or fabric. Enzymatic scouring of textiles has been performed using enzyme systems comprising pectinases.

EP943028 discloses an enzymatic scouring of cotton fabrics at alkaline pH condition. EP1159479 discloses the method of scouring cotton fabrics with an enzyme having thermostable pectate lyase enzymatic activity.

There is always a need in the art to improve bioscouring methods that can be performed effectively to remove non-cellulosic impurities and are also environmentally friendly.

SUMMARY OF THE INVENTION

The present invention relates to a composition and a method for treating a textile.

In one aspect, a composition is provided, comprising a pectinase and a surfactant with chemical structure A and/or a surfactant with chemical structure B:

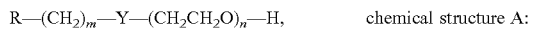    chemical structure A:

wherein R is selected from the group consisting of —H, —CH$_3$, —CH$_2$—CH$_3$, —CH$_2$—CH$_2$—CH$_3$, and —CH—(CH$_3$)$_2$; Y is selected from the group consisting of —CH$_2$— and —CO—O—; 6≤m≤14 and 1≤n≤18;

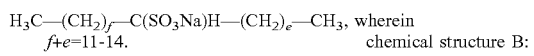    chemical structure B:

In another aspect, the present invention provides a method for scouring textile by treating cellulosic material with a pectinase and a surfactant with chemical structure A and/or a surfactant with chemical structure B:

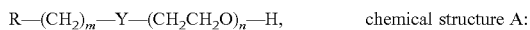    chemical structure A:

wherein R is selected from the group consisting of —H, —CH$_3$, —CH$_2$—CH$_3$, —CH$_2$—CH$_2$—CH$_3$, —CH$_2$—(CH$_3$)$_2$; Y is selected from the group consisting of —CH$_2$—, —CO—O—; 6≤m≤14 and 1≤n≤8;

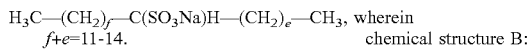    chemical structure B:

DETAILED DESCRIPTION OF THE INVENTION

As used herein, the singular forms "a", "an", and "the" include plural references unless the context clearly dictates otherwise. Thus, for example, references to "a pectinase" include the use of one or more pectinase. "A step" of a method means at least one step, and it could be one, two, three, four, five or even more method steps.

EC-numbers may be used for classification of enzymes. Reference is made to the Recommendations of the Nomenclature Committee of the International Union of Biochemistry and Molecular Biology, Academic Press Inc., 1992.

As used herein, the term "sequential" with reference to a plurality of enzymatic treatments of a textile, means that a second specified enzymatic treatment is performed after a first specified enzymatic treatment is performed. Sequential treatments may be separated by intervening wash steps. Where specified, sequential enzymatic treatments may be performed "in the same bath," meaning in the substantially the same liquid medium without intervening wash steps. Single-bath sequential treatment may include pH adjustments, temperature adjustment, and/or the addition of salts, activators, mediators, and the like, but should not include washes or rinses.

As used herein, the term "simultaneous," with reference to a plurality of enzymatic treatments of a textile, means that a second specified enzymatic treatment is performed at the same time (i.e., at least partially overlapping with) as a first specified enzymatic treatment. Simultaneous enzymatic treatments are necessarily performed "in the same bath" without intervening wash steps.

Pectinases

The term pectinase or pectolytic enzyme is intended to include any pectinase enzyme defined according to the art where pectinases are a group of enzymes that catalyze the cleavage of glycosidic linkages. Basically three types of pectolytic enzymes exist: pectinesterase, which only removes methoxyl residues from pectin, a range of depolymerizing enzymes, and protopectinase, which solubilizes protopectin to form pectin (Sakai et al., (1993) Advances in Applied Microbiology vol 39 pp 213-294). Example of a pectinases or pectolytic enzyme useful in the invention is pectate lyase (EC 4.2.2.2 and EC 4.2.2.9), polygalacturonase (EC 3.2.1.15 and EC 3.2.1.67), polymethyl galacturonase, pectin lyase (EC 4.2.2.10), galactanases (EC 3.2.1.89), arabinanases (EC 3.2.1.99) and/or pectin esterases (EC 3.1.1.11).

Suitable pectinolytic enzymes include those described in WO 99/27083, WO 99/27084, WO 00/55309, WO 02/092741 and WO08039353. One example of commercially available pectolytic enzyme product useful in the method of the present invention is PrimaGreen® EcoScour (available from DuPont Company, U.S.A.).

Preferably, the pectinase used in the present invention is pectate lyase. Suitable pectate lyases include those of bacterial or fungal origin. Chemically or genetically modified mutants are included. In a preferred embodiment the pectate lyase is derived from a strain of the genus *Bacillus*, especially a strain of *Bacillus substilis*, especially *Bacillus subtilis* DSM14218 disclosed in SEQ ID NO:2 or a variant thereof disclosed in Example 6 of WO 02/092741 (hereby incorporated by reference) or a variant disclosed in WO 03/095638 (hereby incorporated by reference). Alternatively the pectate lyase is derived from a strain of *Bacillus licheniformis*, especially the pectate lyases disclosed as SEQ ID NO: 8 in WO 99/27083 or variants thereof as described in WO 02/06442.

Such pectinase especially pectate lyase useful in practicing the present invention can be identified using, e.g., high-throughput screening techniques such as the agar plate screening procedure described in Example 1 below.

For purposes of the present invention, pectinase or pectolytic enzyme activity (especially pectate lyase activity) is the activity determined by measuring the increase in absorbance at 235 nm of a 0.1% w/v solution of sodium polygalacturonate in 0.1M glycine buffer at pH 10. Enzyme activity is typically expressed as x µmol/min, i.e., the amount of enzyme that catalyzes the formation of x µmole product/min.

A neutral petinase or pectolytic enzyme is an enzyme that exhibits maximal enzyme activity at a neutral condition, for example, a pH of from about 6.0 to about 8.0, preferably, about 6.5 to about 7.5, more preferably about 7.0.

Non-limiting examples of pectinase whose use is encompassed by the present invention include polypeptides comprising or consisting of the mature peptide sequence of SEQ ID NO:1 and polypeptides comprising or consisting of amino acid sequences having at least about 60% identity, preferably at least about 70% identity, more preferably at least about 80% identity, more preferably at least about 90% identity, more preferably at least about 95% identity, more preferably at least about 96% identity, more preferably at least about 97% identity, more preferably at least about 98% identity, more preferably at least about 99% identity, and most preferably 100% identity with SEQ ID NO:1.

In a preferred embodiment, the pectinase of the method and composition of the invention comprises or consists of an amino acid sequence with a substitution, deletion, and/or insertion of one or more (or several) amino acids of the mature polypeptide of SEQ ID NO: 1. Pectinase of SEQ ID NO: 1 is a pectate lyase from *Bacillus licheniformis*. The mature peptide of SEQ ID NO: 1 is amino acids 28-341.

For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment– Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment–Total Number of Gaps in Alignment)

In the present invention, the polypeptide sequence of the pectate lyase can be variants comprising a substitution, deletion, and/or insertion of one or more (or several) amino acids of the polypeptide of SEQ ID NO: 1, or a homologous sequence thereof. Preferably, amino acid changes (i.e. substitution, deletion, and/or insertion of one or more (or several) amino acids) are of a minor nature, that is conservative amino acid substitutions or insertions that do not significantly affect the folding and/or activity of the protein; small deletions, typically of one to about 30 amino acids; small amino or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for endoglucanse activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to the parent polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241:

53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Preferably, the total number of amino acid substitutions, deletions and/or insertions of the polypeptide of SEQ ID NO: 1 is not more than 10, e.g., 1, 2, 3, 4, 5, 6, 7, 8 or 9.

The polypeptide may be hybrid polypeptide in which a portion of one polypeptide is fused at the N-terminus or the C-terminus of a portion of another polypeptide.

The polypeptide may be a fused polypeptide or cleavable fusion polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, Drug Discovery World 4: 35-48.

Surfactants

The composition and the method of the present invention comprise a pectinase and a surfactant with chemical structure A and/or a surfactant with chemical structure B:

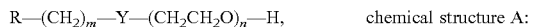

R—(CH$_2$)$_m$—Y—(CH$_2$CH$_2$O)$_n$—H,     chemical structure A:

wherein R is selected from the group consisting of —H, —CH$_3$, —CH$_2$—CH$_3$, —CH$_2$—CH$_2$—CH$_3$, —CH$_2$—(CH$_3$)$_2$; Y is selected from the group consisting of —CH$_2$—, —CO—O—; 6≤m≤14 and 1≤n≤8;

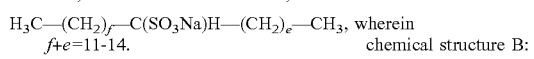

H$_3$C—(CH$_2$)$_f$—C(SO$_3$Na)H—(CH$_2$)$_e$—CH$_3$, wherein
$f+e=11-14$.     chemical structure B:

In another embodiment, the composition or method of the present invention further comprises other surfactants selected from nonionic and/or anionic and/or cationic and/or ampholytic and/or zwitterionic and/or semi-polar surfactants.

In another embodiment, the composition or method of the present invention further comprises SAP (Dioctyl sodium sulfosuccinate).

Preferred systems to be used according to the present invention comprise as a surfactant one or more of the nonionic and/or anionic surfactants described herein.

Polyethylene, polypropylene, and polybutylene oxide condensates of alkyl phenols are suitable for use as the nonionic surfactant of the surfactant systems of the present invention, with the polyethylene oxide condensates being preferred. The condensation products of primary and secondary aliphatic alcohols with about 1 to about 25 moles of ethylene oxide are suitable for use as the nonionic surfactant of the nonionic surfactant systems of the present invention. Also useful as the nonionic surfactant of the surfactant systems of the present invention are alkylpolysaccharides disclosed in U.S. Pat. No. 4,565,647. The condensation products of ethylene oxide with a hydrophobic base formed by the condensation of propylene oxide with propylene glycol are also suitable for use as the additional nonionic surfactant systems of the present invention. Also suitable for use as the nonionic surfactant of the nonionic surfactant system of the present invention, are the condensation products of ethylene oxide with the product resulting from the reaction of propylene oxide and ethylenediamine.

Highly preferred anionic surfactants include alkyl alkoxy-lated sulfate surfactants and the analogous phosphate esters. Suitable anionic surfactants to be used are alkyl ester sulfonate surfactants including linear esters of C8-C20 carboxylic acids (i.e., fatty acids) which are sulfonated with gaseous SO$_3$ according to "The Journal of the American Oil Chemists Society", 52 (1975), pp. 323-329. Other anionic surfactants useful for textile cleaning purposes can also be included in the aqueous compositions of the present invention. The aqueous compositions of the present invention may also contain cationic, ampholytic, zwitterionic, and semi-polar surfactants, as well as the nonionic and/or anionic surfactants other than those already described herein.

In some embodiments of the invention, the composition for textile manufacturing further comprises other component, including without limitation additional enzymes, as well as bleaching agents, antifoaming agents, builder systems, and the like, that enhance the scouring process and/or provide superior effects related to, e.g., bleachability, strength, resistance to pilling, water absorbency, and dyeability.

Textile

As used herein, the term "textile" refers to fibers, yarns, fabrics (for example, wovens, non-wovens or knits), and garments. The term encompasses textiles made from natural, synthetic (e.g., manufactured), and various natural and synthetic blends. Textiles may be unprocessed or processed fibers, yarns, woven or knit fabrics, non-wovens, and garments and may be made using a variety of materials, some of which are mentioned, herein.

The process of the invention is most beneficially applied to cellulose-containing textile, including fabrics, such as cotton, viscose, rayon, ramie, linen, Tencel, or mixtures thereof, or mixtures of any of these fibres, or mixtures of any of these fibres together with synthetic fibres such as mixtures of cotton and spandex (stretch-denim).

Preferably, the textile of the present invention is made from pure cellulose or is made from blends of cellulose fibers and any other materials conventionally used for making textile such as poly (ethylene terephthalate), wool, and silk.

In a preferred embodiment the cellulose-containing textile is a textile blend comprising more than 30% (w/w) of cellulose, in particular more than 35%, more than 50%, more than 65%, more than 90%, or more than 95% of cellulose. In an even preferred embodiment, the process of the invention is applied to textile consisting essentially of cellulose, i.e. pure cellulose textile, such as pure cotton textile. In particular, the fabric is undyed fabric.

Additional Enzymes

It will be appreciated that one or more cellulase, amylase, lipase, mannanase, xylanase, protease, oxidase, catalase, cutinase or other enzyme mentioned, herein, may be used as additional enzyme in the present compositions and methods. Moreover, any number of additional enzymes (or enzyme systems) can be combined with the present compositions and methods without defeating the spirit of the disclosure.

Proteases

In a preferred embodiment, proteases are used in the present invention. Suitable proteases include those of animal, vegetable or microbial origin. Microbial origin is preferred. Chemically modified or protein engineered mutants are included. The protease may for example be a metalloprotease (EC 3.4.17 or EC 3.4.24) or a serine protease (EC 3.4.21), preferably an alkaline microbial protease or a trypsin-like protease. Examples of proteases are subtilisins (EC 3.4.21.62), especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Preferred commercially available protease enzymes include Alcalase®, Savinase®, Primase®, Duralase®, Esperase®, and Kannase® (Novozymes A/S), Maxatase®, Maxacal®, Maxapem®, Properase®, Purafect®, Purafect OxP®, FN2™, and FN3™ (available from Danisco A/S).

Lipases

In other embodiments of the present invention, lipases are used in the present invention. Suitable lipases include those of bacterial or fungal origin. Chemically or genetically modified mutants of such lipases are included in this connection. The lipase may for example be triacylglycerol lipase (EC3.1.1.3), phospholipase A2 (EC 3.1.1.4), Lysophospholipase (EC 3.1.1.5), Monoglyceride lipase (EC 3.1.1.23), galactolipase (EC 3.1.1.26), phospholipase A1 (EC 3.1.1.32), Lipoprotein lipase (EC 3.1.1.34). Examples of useful lipases include a *Humicola lanuginosa* lipase, e.g., as described in EP 258 068 and EP 305 216; a *Rhizomucor miehei* lipase, e.g., as described in EP 238 023 or from *H. insolens* as described in WO 96/13580; a *Candida* lipase, such as a *C. antarctica* lipase, e.g., the *C. antarctica* lipase A or B described in EP 214 761; a *Pseudomonas* lipase, such as one of those described in EP 721 981 (e.g., a lipase obtainable from a *Pseudomonas* sp. SD705 strain having deposit accession number FERM BP-4772), in PCT/JP96/00426, in PCT/JP96/00454 (e.g., a *P. solanacearum* lipase), in EP 571 982 or in WO 95/14783 (e.g., a *P. mendocina* lipase), a *P. alcaligenes* or *P. pseudoalcaligenes* lipase, e.g., as described in EP 218 272, a *P. cepacia* lipase, e.g., as described in EP 331 376, a *P. stutzeri* lipase, e.g., as disclosed in GB 1,372,034, or a *P. fluorescens* lipase; a *Bacillus* lipase, e.g., a *B. subtilis* lipase (Dartois et al. (1993) Biochemica et Biophysica Acta 1131:253-260), a *B. stearothermophilus* lipase (JP 64/744992) and a *B. pumilus* lipase (WO 91/16422).

Suitable commercially available lipases include Lipex®, Lipolase® and Lipolase Ultra®, Lipolex®, Lipoclean® (available from Novozymes A/S), M1 Lipase™ and Lipomax™ (available from Danisco A/S) and Lipase P "Amano" (available from Amano Pharmaceutical Co. Ltd.).

Amylases

In other embodiments, amylases are used in the present invention. Amylases comprise e.g., alpha-amylases (EC 3.2.1.1), beta-amylases (EC 3.2.1.2) and/or glucoamylases (EC 3.2.1.3) of bacterial or fungal origin. Chemically or genetically modified mutants of such amylases are included in this connection. Alpha-amylases are preferred in relation to the present invention. Relevant alpha-amylases include, for example, α-amylases obtainable from *Bacillus* species, in particular a special strain of *B. licheniformis*, described in more detail in GB 1296839.

Further examples of useful amylases are the alpha-amylases derived from *Bacillus* sp. he AA560 alpha-amylase derived from *Bacillus* sp. DSM 12649 disclosed as SEQ ID NO: 2 in WO 00/60060 (hereby incorporated by reference) and the variants of the AA560 alpha-amylase, including the AA560 variant disclosed in Example 7 and 8 (hereby incorporated by reference).

Relevant commercially available amylases include Natalase®, Stainzyme®, Duramyl®, Termamyl®, Termamyl™ Ultra, Fungamyl® and BAN® (all available from Novozymes A/S, Bagsvaerd, Denmark), and Rapidase® and Maxamyl® P (available from DSM, Holland) and Purastar®, Purastar OxAm and Powerase™ (available from Danisco A/S).

Other useful amylases are CGTases (cyclodextrin glucanotransferases, EC 2.4.1.19), e.g., those obtainable from species of *Bacillus*, *Thermoanaerobactor* or *Thermoanaerobacterium*.

Hemicellulases

In other embodiments, hemicellulases are used in the present invention. Hemicelluloses are the most complex group of non-starch polysaccharides in the plant cell wall. They consist of polymers of xylose, arabinose, galactose, mannose and/or glucose which are often highly branched and connected to other cell wall structures. Hemicellulases of the present invention therefore include enzymes with xylanolytiactivity, arabinolytic activity, galactolytic activity and/or mannolytic activity. The hemi-cellulases of the present invention may for example be selected from xylanases (EC 3.2.1.8, EC 3.2.1.32, and EC 3.2.1.136), xyloglucanases (EC 3.2.1.4 and EC 3.2.1.151), arabinofuranosidases (EC 3.2.1.55), acetylxylan esterases (EC 3.1.1.72), glucuronidases (EC 3.2.1.31, EC 3.2.1.56, 3.2.1.128 and 3.2.1.139), glucanohydrolase (EC 3.2.1.11, EC 3.2.1.83 and EC 3.2.1.73), ferulic acid esterases (EC 3.1.1.73), coumaric acid esterases (EC 3.1.1.73), mannanases (EC 3.2.1.25; EC 3.2.1.78 and EC 3.2.1.101), arabinosidase (EC 3.2.1.88), arabinanases (EC 3.2.1.99), galactanases (EC 3.2.1.89, EC 3.2.1.23 and 3.2.1.164) and lichenases (EC 3.2.1.73). This is, however, not to be considered as an exhausting list.

Mannananase is a preferred hemicellulase in relation to the present invention. Mannanases hydrolyse the biopolymers made up of galactomannans. Mannan containing stains often comprise guar gum and locust bean gum, which are widely used as stabilizers in food and cosmetic products. Suitable mannanases include those of bacterial or fungal origin. Chemically or genetically modified mutants are included. In a preferred embodiment the mannanase is derived from a strain of the genus *Bacillus*, especially *Bacillus* sp. 1633 disclosed in positions 31-330 of SEQ ID NO:2 or in SEQ ID NO: 5 of WO 99/64619 (hereby incorporated by reference) or *Bacillus agaradhaerens*, for example from the type strain DSM 8721. A suitable commercially available mannanase is Mannaway® produced by Novozymes A/S Denmark or Purabrite™ produced by Dupont USA.

Xylanase is a preferred hemicellulase in relation to the present invention. A suitable commercially available xylanase is Pulpzyme® HC (available from Novozymes A/S).

Cellulases

The composition and method of the present invention may further include cellulase defined in the present invention. In the present context, the term "cellulase" or "cellulolytic enzyme" refers to an enzyme which catalyzes the degradation of cellulose to glucose, cellobiose, triose and other cello-oligosaccharides which enzyme is understood to include a mature protein or a precursor form thereof or a functional fragment thereof, e.g., a catalytic active module, which essentially has the activity of the full-length enzyme. Furthermore, the term "cellulolytic" enzyme is intended to include homologues or analogues of said enzyme. Suitable cellulases include those of animal, vegetable or microbial origin. Microbial origin is preferred. The cellulolytic enzyme may be a component occurring in a cellulase system produced by a given microorganism, such a cellulase system mostly comprising several different cellulase enzyme components including those usually identified as, e.g., cellobiohydrolases, endoglucanases, and beta-glucosidases. In a preferred embodiment the cellulase is an endoglucanase.

Examples of commercially available cellulase enzyme products useful in the method of the present invention are: Cellusoft CR®, Cellusoft L®, Novoprime A 378® (all available from Novozymes A/S, Denmark); Indiage™, Primafast™ (both from Dupont company, U.S.A.); Ecostone™ (from Alko, Finland); Rocksoft™ (from CPN, U.S.A.), and Sanko Bio™ (from Meiji/Rakuto Kasei Ltd., Japan).

Textile Manufacturing Process

The processing of a fabric, such as of a cellulosic material, into material ready for garment manufacture involves several steps: spinning of the fiber into a yarn; construction of woven or knit fabric from the yarn; and subsequent preparation processes, dyeing/printing and finishing operations. Preparation processes are necessary for removing natural and man-induced impurities from fibers and for improving their aesthetic appearance and processability prior to for instance dyeing/printing and finishing. Common preparation processes comprise desizing (for woven goods), scouring, and bleaching, which produce a fabric suitable for dyeing or finishing.

Woven fabric is constructed by weaving "filling" or "weft" yarns between warp yarns stretched in the longitudinal direction on the loom. The warp yarns must be sized before weaving in order to lubricate and protect them from abrasion at the high speed insertion of the filling yarns during weaving. Common size agents are starches (or starch derivatives and modified starches), poly(vinyl alcohol), carboxyl methyl cellulose (i.e. CMC) where starches are dominant. Paraffin, acrylic binders and variety of lubricants are often included in the size mix. The filling yarn can be woven through the warp yarns in a "over one—under the next" fashion (plain weave) or by "over one—under two" (twill) or any other myriad of permutations. Generally, dresses, shirts, pants, sheeting's, towels, draperies, etc. are produced from woven fabric. After the fabric is made, size on the fabric must be removed again (i.e. desizing).

Knitting is forming a fabric by joining together interlocking loops of yarn. As opposed to weaving, which is constructed from two types of yarn and has many "ends", knitted fabric is produced from a single continuous strand of yarn. As with weaving, there are many different ways to loop yarn together and the final fabric properties are dependent both upon the yarn and the type of knit. Underwear, sweaters, socks, sport shirts, sweat shirts, etc. are derived from knit fabrics.

Desizing

Desizing is the degradation and/or removal of sizing compounds from warp yarns in a woven fabric. Starch is usually removed by an enzymatic desizing procedure. In addition, oxidative desizing and chemical desizing with acids or bases are sometimes used.

In some embodiments, the desizing enzyme is an amylolytic enzyme, such as an alpha-amylase, a beta-amylase, a mannanase, a glucoamylase, or a combination thereof.

Suitable alpha and beta-amylases include those of bacterial or fungal origin, as well as chemically or genetically modified mutants and variants of such amylases. Suitable alpha-amylases include alpha-amylases obtainable from *Bacillus* species. Suitable commercial amylases include but are not limited to OPTISIZE® NEXT, OPTISIZE® FLEX and OPTISIZE® COOL (all from Dupont company USA), and DURAMYL™, ERMAMYL™, FUNGAMYL™ TERMAMYL™, AQUAZYME™ and BAN™ (all available from Novozymes A/S, Bagsvaerd, Denmark).

Other suitable amylolytic enzymes include the CGTases (cyclodextrin glucanotransferases, EC 2.4.1.19), e.g., those obtained from species of *Bacillus, Thermoanaerobactor* or *Thermoanaero-bacterium*.

Scouring

Scouring is used to remove impurities from the fibers, to swell the fibers and to remove seed coat fragments. It is one of the most critical steps. The main purposes of scouring is to a) uniformly clean the fabric, b) soften the motes and other trashes, c) improve fabric absorbency, d) saponify and solubilize fats, oils, and waxes, and e) minimize immature cotton. Sodium hydroxide scouring at about boiling temperature is the accepted treatment for 100% cotton, while calcium hydroxide and sodium carbonate are less frequently used. Synthetic fibers are scoured at much milder conditions. Surfactant and chelating agents are essential for alkaline scouring. Enzymatic scouring has been introduced, wherein cellulase, hemicellulase, pectinase, lipase, and protease are all reported to have scouring effects.

Bleaching

Bleaching is the destruction of pigmented color and/or colored impurities as well as seed coat fragment removal. Bleaching is performed by the use of oxidizing or reducing chemistry. Oxidizing agents can be further subdivided into those that employ or generate: a) hypochlorite ($OCl^-$), b) chloride dioxide ($ClO_2$), c) permanganate ($MnO_4-$), d) ozone, and hydroperoxide species ($OOH^-$ and/or $OOH$). Reducing agents are typical sulfur dioxide, hydrosulfite salts, etc. Enzymatic bleaching using glucose oxidase or peroxidase (for example, see WO 2013/040991) has been reported. Traditionally, hydrogen peroxide is used in this process.

Printing and Dyeing

Printing and dyeing of textiles is carried out by applying dyes to the textile by any appropriate method for binding the dyestuff to the fibres in the textiles. The dyeing of textiles may for example be carried out by passing the fabric through a concentrated solution of dye, followed by storage of the wet fabric in a vapour tight enclosure to permit time for diffusion and reaction of the dye with the fabric substrate prior to rinsing off un-reacted dye. Alternatively, the dye may be fixed by subsequent steaming of the textile prior to rinsing. The dyes include synthetic and natural dyes. Typical dyes are those with anionic functional groups (e.g. acid dyes, direct dyes, Mordant dyes and reactive dyes), those with cationic groups (e.g. basic dyes), those requiring chemical reaction before application (e.g. vat dyes, sulphur dyes and azoic dyes), disperse dyes and solvent dyes.

Excess soluble dyestuff not bound to the fibres must be removed after dyeing to ensure fastness of the dyed textiles and to prevent unwanted dye transfer during laundering of the textiles by the consumer. Generally, a large amount of water is required for complete removal of excess dye. In a conventional process, the printed or dyed textile is first rinsed with cold water, then washed at high temperature with the addition of a suitable additive to decrease back-staining, like poly(vinylpyrrolidone) (PVP).

An enzymatic process for removal of excess dye from dyed fabric with a rinse liquor comprising at least one peroxidase, an oxidizing agent and at least one mediator, such as liquor comprising a peroxidase, hydrogen peroxidise and a mediator like 1-hydroxy-benzotriazole is disclosed in WO99/34054.

Biopolishinq

As used herein, the term "biopolishing", "depilling" and "anti-pilling" are interchangeable.

Most cotton fabrics and cotton blend fabrics have a hand-feeling problem that is rather hard and stiff without the application of finishing components. The fabric surface also is not smooth because small fuzzy microfibrils protrude from it. In addition, after a relatively short period of wear, pilling appears on the fabric surface thereby giving it an unappealing, worn look.

Biopolishing is a method to treat cellulosic fabrics during their manufacture by enzymes such as cellulases, which improves fabric quality with respect to "reduced pilling formation". The most important effects of biopolishing can be characterized by less fuzz and pilling, increased gloss/luster, improved fabric handle, increased durable softness and/or improved water absorbency. Biopolishing usually takes place in the wet processing of the manufacture of knitted and woven fabrics or garments. Wet processing comprises such steps as e.g., desizing, scouring, bleaching, washing, dying/printing and finishing. Biopolishing could be performed as a separate step after any of the wetting steps or in combination with any of those wetting steps.

Composition for Textile Treatment

The present invention further relates to a composition for textile treatment comprising a pectinase and a surfactant with chemical structure A and/or a surfactant with chemical structure B.

In the present invention, the ratio of pectinase to surfactant with structure A and/or chemical structure B is in the range of from about 1:1000 to about 1:500, preferably in the range of from about 1:300 to about 1:500 (w/w).

The textile composition may be adapted for specific uses, such as scouring, which can provide at least one of the textile benefits such as increased pectin removal, increased wettability, and increased desizing value as measured by TEGEWA assay.

The textile composition may further include one or more of the enzymes selected from the group consisting of cellulase, amylase, lipase, mannanase, xylanase, protease, oxidase, catalase and cutinase.

The textile composition typically comprises conventional ingredients including without limitation other enzymes, as well as surfactants, stabilizer, wetting agent, dispersing agents, antifoaming agents, lubricants, builder systems, and the like, or a mixture thereof.

The textile composition can be in any form, such as a solid, liquid, paste, gel or any combination thereof. Preferably, the composition is in the form of a liquid.

Method of the Invention

In the present invention, a method of treating textile with a pectinase and a surfactant with chemical structure A and/or a surfactant with chemical structure B is provided.

A suitable liquor/textile ratio to be used in the present method may be in the range of from about 20:1 to about 2:1, preferably in the range of from about 18:1 to about 4.5:1, more preferably in the range of from 15:1 to 4:1 (volume/weight ml/g), most preferably in the range of from 10:1 to 4:1.

The reaction time is usually in the range of from about 5 minute to about 2 hours. Preferably the reaction time is within the range of from about 10 minutes to about 60 minutes, more preferably the reaction time is within the range of from about 15 minutes to about 60 minutes, even more preferably within 15 to 30 minutes.

The process of the present invention is carried out at a pH of from about 5 to about 10, preferably at a pH from about 5.5 to about 10, more preferably at a pH from about 6 to about 8, even more preferably at a pH from about 7.

In some embodiments, the process of the present invention is conducted at the temperature range of 20-90° C., preferably 30-80° C., more preferably 40-70° C., more preferably 50-60° C.

Enzyme dosage greatly depends on the enzyme reaction time and enzyme activity, i.e. a relatively short enzymatic reaction time or low enzymatic activity necessitates a relatively increased enzyme dosage, and vice versa. In general, enzyme dosage may be stipulated in accordance with the reaction time available.

In a particular embodiment, the dosage of the pectinase is from about 0.005 milligram (mg) enzyme protein to about 200 mg enzyme protein (of each enzyme) per gram of textile, preferably 0.008 mg enzyme protein to 100 mg enzyme protein per gram of textile, more preferably 0.01 mg enzyme protein to 50 mg enzyme protein per gram of textile, more preferably 0.01 mg enzyme protein to 1 mg enzyme protein per gram of textile. Again, these amounts refer to the amount of each enzyme.

In an embodiment, the dosage of the additional enzymes, if any, is from about 0.005 milligram (mg) enzyme protein to about 200 mg enzyme protein (of each enzyme) per gram of textile, preferably 0.008 mg enzyme protein to 100 mg enzyme protein per gram of textile, more preferably 0.01 mg enzyme protein to 50 mg enzyme protein per gram of textile, more preferably 0.01 mg enzyme protein to 1 mg enzyme protein per gram of textile. Again, these amounts refer to the amount of each enzyme.

According to the invention, a surfactant with chemical structure A and/or a surfactant with chemical structure B may be present in a concentration in the range of from 0.01 mM to 100 mM, preferably in the range of from 0.1 mM to 50 mM, more preferably in the range of from 0.5 mM to 20 mM, and even more preferably in the range of from 1 mM to 10 mM.

In the process of the invention, the pectinase may be applied alone or together with an additional enzyme. The term "an additional enzyme" means at least one additional enzyme, e.g. one, two, three, four, five, six, seven, eight, nine, ten or even more additional enzymes.

The term "applied together with" (or "used together with") means that the additional enzyme may be applied in the same, or in another step of the process of the invention. The other process step may be upstream or downstream in the textile manufacturing process, as compared to the step in which the textile is treated with a pectinase.

In particular embodiments the additional enzyme is an enzyme which has cellulase, amylase, lipase, mannanase, xylanase, protease, oxidase, catalase, cutinase or other enzyme mentioned. In a preferred embodiment, the additional enzyme is cellulase.

In some embodiments, the method for treating textile comprises (a) desizing the textile; (b) scouring the textile with a pectinase and a surfactant with chemical structure A and/or a surfactant with chemical structure B. In some embodiments, between step (a) and step (b), there is a wash step. In some embodiments, step (a) and step (b) are performed in a single bath without intervening wash steps. In some embodiments, step (a) and step (b) are performed sequentially or simultaneously in the same bath. In some embodiments, step (a) and step (b) are performed sequentially in a single bath, wherein step (a) is performed prior to step (b).

The invention is further defined in the following paragraphs:

[1]. A composition, comprising a pectinase and a surfactant with chemical structure A and/or a surfactant with chemical structure B:

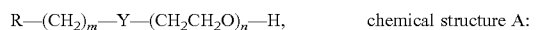

chemical structure A:

wherein R is selected from the group consisting of —H, —CH$_3$, —CH$_2$—CH$_3$, —CH$_2$—CH$_2$—CH$_3$, and —CH—(CH$_3$)$_2$; Y is selected from the group consisting of —CH$_2$— and —CO—O—; 6≤m≤14 and 1≤n≤18;

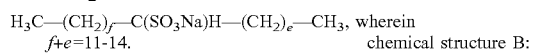

chemical structure B:

[2]. The composition of paragraph 1, wherein the composition comprising a pectinase and a surfactant with chemical structure A.

[3]. The composition of paragraph 2, wherein the composition comprising a pectinase and a surfactant with chemical structure A and a surfactant with chemical structure B.

[4]. The composition of any of paragraphs 1-3, wherein R is —CH—(CH$_3$)$_2$ and Y is —CH$_2$—.

[5]. The composition of any of paragraphs 1-3, wherein R is —CH$_3$ and Y is —CO—O—.

[6]. The composition of any of paragraphs 1-5, wherein m is 9.

[7]. The composition of any of paragraphs 1-6, wherein n is 5, 6, 8, 10 or 12.

[8]. The composition of any of paragraphs 1-7, wherein further comprises surfactant SAP.

[9]. The composition of any of paragraphs 1-8, wherein the pectinase is a pectate lyase; preferably a neutral pectate lyase; or preferably, the pectinase comprises or consists of amino acid sequences having at least about 60% identity, preferably at least about 70% identity, more preferably at least about 80% identity, more preferably at least about 90% identity, more preferably at least about 95% identity, more preferably at least about 96% identity, more preferably at least about 97% identity, more preferably at least about 98% identity, more preferably at least about 99% identity, and most preferably 100% identity with SEQ ID NO:1.

[10]. The composition of any of paragraphs 1-9, wherein the composition further comprises a cellulase.

[11]. The composition of any of paragraphs 1-10, wherein the composition further comprises amylase.

[12]. The composition of any of paragraphs 1-11, wherein the composition further comprises one or more enzymes selected from the group consisting of lipase, mannanase, xylanase, protease, oxidase, catalase and cutinase.

[13]. A method for scouring of cellulosic material, comprising treating cellulosic material with a pectinase and a surfactant with chemical structure A and/or a surfactant with chemical structure B:

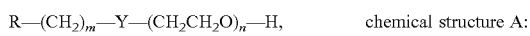

chemical structure A:

wherein R is selected from the group consisting of —H, —CH$_3$, —CH$_2$—CH$_3$, —CH$_2$—CH$_2$—CH$_3$, and —CH—(CH$_3$)$_2$; Y is selected from the group consisting of —CH$_2$— and —CO—O—; 6≤m≤14 and 1≤n≤18;

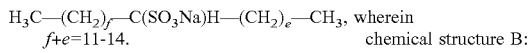

chemical structure B:

[14]. The method of paragraph 13, comprising treating cellulosic material with a pectinase and a surfactant with chemical structure A.

[15]. The method of paragraph 14, comprising treating cellulosic material with a pectinase and a surfactant with chemical structure A and a surfactant with chemical structure B.

[16]. The method of any of paragraphs 13-15, wherein R is —CH—(CH$_3$)$_2$ and Y is —CH$_2$—.

[17]. The method of any of paragraphs 13-15, wherein R is —CH$_3$ and Y is —CO—O—.

[18]. The composition of any of paragraphs 13-17, wherein m is 9.

[19]. The composition of any of paragraphs 13-18, wherein n is 5, 6, 8, 10 or 12.

[20]. The method of any of paragraphs 13-19, further comprising treating the cellulosic material with surfactant SAP.

[21]. The method of any of paragraphs 13-20, wherein the pectinase is a pectate lyase; preferably a neutral pectate lyase.

[22]. The method of any of paragraphs 13-21, further comprising treating the cellulosic material with a cellulase.

[23]. The method of any of paragraphs 13-22, further comprising treating the cellulosic material with an amylase.

[24] The method of any of paragraphs 13-23, further comprising treating the cellulosic material with one or more enzymes selected from the group consisting of lipase, mannanase, xylanase, protease, oxidase, catalase and cutinase.

[25]. The method of any of paragraphs 13-24, wherein the cellulosic material is textile, preferably the cellulosic material is fiber, yarn, fabric, garment; more preferably the cellulosic material is fabric including woven, non-woven, or knits.

[26]. A method for treating textile, comprising
(a) desizing the textile with an amylase;
(b) scouring the textile with a pectinase and a surfactant with chemical structure A and/or a surfactant with chemical structure B.

[27]. The method of paragraph 26, wherein a wash step is between step (a) and (b).

[28]. The method of paragraph 26, wherein step (a) and step (b) are performed in a single bath without intervening wash steps.

[29]. The method of paragraph 26, wherein step (a) and step (b) are performed sequentially or simultaneously in the same bath.

[30]. The method of any of paragraphs 26-29, wherein cellulase is further added before, during or after step (a) or step (b).

The present invention is further described by the following examples that should not be construed as limiting the scope of the invention.

EXAMPLES

Materials & Methods

Enzymes:

Pectinase-A: mature peptide of a *Bacillus licheniformis* pectate lyase with SEQ ID NO: 1 (described in U.S. Pat. No. 6,187,580)

Cellulase-C: a *Thielavia terrestis* cellulase with SEQ ID NO: 2 (described in WO98/12307)

Aquazyme SD-L: an amylase product commercially available from Novozymes A/S.

Chemicals:

Leophen FR-M: a surfactant commercially available from BASF company.

Kieralon® Wash F-OLB Conc (abbreviated as F-OLB): a surfactant commercially available from BASF company.

Prestogen® PL: $H_2O_2$ stabilizer, commercially available from BASF company.

SAP (Dioctyl sodium sulfosuccinate): an anionic surfactant commercially available from Jiangsu Haian Petrochemical Plant, China.

SAS60 (Secondary Alkane Sulfonate): an anionic surfactant commercially available from BASF company.

X-NF: a surfactant commercially available from Zhanfeng chemicals company.

FMFD: a surfactant commercially available from Zhanfeng chemicals company.

Surfactants:

TABLE 1

Chemical structure A: $R-(CH_2)_m-Y-(CH_2CH_2O)_n-H$

| | | | Surfactant | | | | | |
|---|---|---|---|---|---|---|---|---|
| IPE1305 | IPE1306 | IPE1308 | IPE1310 | IPE1312 | DGM | TGM | HGM | OGM |
| m = | | 9 | | | | | | |
| n = 5 | 6 | 8 | 10 | 12 | 2 | 4 | 6 | 8 |
| Y = | | $-CH_2-$ | | | | $-CO-O-$ | | |
| R = | | $-CH-(CH_3)_2$ | | | | $-CH_3$ | | |

TABLE 2

Chemical structure B: $H_3C-(CH_2)_f-C(SO_3Na)H-(CH_2)_e-CH_3$

| Chemical name | SAS60 (Secondary Alkane Sulfonate) |
|---|---|
| f + e = | 11-14 |

Wettability Measurement

Wetting time (for woven and knitted fabric): the smaller wetting time value corresponds to a better wettability.

1) Prepare test samples of suitable size of 70 mm×70 mm. Avoid creased or folded places in the fabric. After receipt handle the fabric as little as possible and do not sharply fold, iron or treat it in any way. Unless otherwise agreed (e.g. not enough fabric) take three test samples from different places of the fabric to represent it as fully as possible.
2) Fill the pipette with de-mineralised water.
3) Place the test sample in a horizontal position over the beaker.
4) Allow 100 μl water to fall from the pipette onto the test sample and start the stopwatch at this instant.
5) When the diffuse reflection from the liquid vanishes and the liquid is no longer visible above the surface of the fabric, stop the watch and note the time in the laboratory book. Care must be taken not to move the test sample during this time.

This test should be carried out at least 3 times at different areas (and possibly also different test samples). However, make sure that no test area has a centre nearer than 25 mm to that of any area previously tested.

Wicking value (For woven fabric): the larger the wicking value corresponds to a better wettability.

1) Fill the beaker about half way (at least 5 cm above bottom of glass).
2) Place the top of the swatch (or yarn) in the center of the thermometer clamp, so that the line is at the bottom of the clamp.
3) Adjusting the clamp until the surface of the dye solution is even with the line at the bottom of the fabric (or yarn). Start the timer as soon as the swatch is in place.
4) Measure the height that the dye solution has wicked up from the surface of the dye solution after 30 minutes and record the height.
5) Repeat test 2 times for each treatment at each direction, as fabric supply allows.
6) Average wicking results for samples from the same treatment.
7) Record all the test results in the laboratory book.

Wetting time (for yarn): a certain amount of yarn was put into a cup of water. The time for the deposits of the yarn was recorded as the wetting time.

TEGEWA Measurement (for Woven Fabric)

TEGEWA rating methodology for testing the fabric desizing rate, the larger TEGEWA value corresponds to the higher desizing rate.

1) Preparation of the iodine solution
   Dissolve 10 g of potassium iodide in 100 ml of water, add 0.65 g of iodine and shake up to complete dissolution, fill with water up to 800 ml and then with ethanol up to 1 liter.
2) Preparation of samples
   Cut the fabric with cutter. For each fabric, two samples are needed.
3) Testing procedure
   Put the fabric sample 1 minute into the iodine solution, rinse 20 second with cold water, dab with filter paper (starch-free) and compare immediately with the violet scale.
4) Make a record about the result according to the study plan, and test the other samples according to step 3.

Whiteness Measurement

Whiteness of the bleached swatches was measured by datacolor SF450X spectrophotometer.

Protein Content

The enzyme protein in an enzyme product can be measured with BCA™ Protein Assay Kit (product number 23225, commercial available from Thermo Fisher Scientific Inc.) according to the product manual.

Example 1: Determination of Pectinase Activity

The following methods are used to characterize pectinase enzymatic activity.

1. Pectinase Assay:

For this assay, a 0.1% sodium polygalacturonate (Sigma P-1879) solution is prepared in in 0.1 M glycine buffer, pH 10. 4 ml of this solution are preincubated for 5 minutes at 40° C. Then, 250 µl of the enzyme (or enzyme dilution) are added, after which the reaction is mixed for 10 seconds on a mixer at the highest speed and incubated for 20 minutes at 40° C. or at another temperature, after which the absorbance at 235 nm is measured using a 0.5 ml cuvette with a 1 cm light path on a HP diode array spectrophotometer in a temperature controlled cuvette holder with continuous measurement of the absorbance at 235 nm. For steady state a linear increase for at least 200 seconds was used for calculation of the rate.

For calculation of the catalytic rate, an increase of 5.2 $A_{235}$ per minutes corresponds to formation of 1 µmol of unsaturated product (Nasuna et al., *J. Biol. Chem.* 241:5298-5306, 1966; and Bartling et al., *Microbiology,* 141:873-881, 1995).

2. Agar Assay:

Pectate lyase activity can be measured by applying a test solution to 4 mm holes punched out in agar plates (such as, for example, LB agar), containing 0.7% w/v sodium polygalacturonate (Sigma P 1879). The plates are then incubated for 6 hours at a particular temperature (such as, e.g., 75° C.). The plates are then soaked in either (i) 1M $CaCl_2$ for 0.5 hour or (ii) 1% mixed alkyl trimethylammonium Br (MTAB, Sigma M-7635) for 1 hour. Both of these procedures cause the precipitation of polygalacturonate within the agar. Pectate lyase activity can be detected by the appearance of clear zones within a background of precipitated polygalacturonate. Sensitivity of the assay is calibrated using dilutions of a standard preparation of pectate lyase.

Pectate lyase-A used in the Examples of the present invention showed clear zones under the above agar assay, which means it has pectate lyase activity.

Example 2: Bioscouring on Knitted Fabric Using Different Surfactants

Knitted fabric: 36S (S represents the count of yarn weaving knitted fabric, the higher count represents higher fabric quality)

knitted fabrics were cut into 25 cm×25 cm and weighted.

Liquor ratio: 10:1

Bioscouring Process:

90 ml $H_2O$ was added into 200 ml Lab-O-Mat tube and surfactants and enzymes were added according to table 3, based on the calculation of actual fabric weights, to make a total volume around 100 ml, which would create a liquid to fabric ratio of 10:1 (v/w, ml/g). Afterward, the prepared fabric was put into reaction liquid and mixed. When above step was finished, all tubes were fixed to the Lab-O-Mat and set procedure at 55° C. for 15 minutes and then 80° C. for 10 minutes. Once above procedure was terminated, all tubes were removed and each sample was rinsed at 50° C. running water for 30 seconds. Particularly, each sample was rinsed separately. All swatches were dried at 105° C. for 30 minutes and then wetting time was measured as above described.

Table 3 shows that heterogeneous ether surfactants IPE1305, IPE1306, IPE1308 and IPE1312 can give good wettability and wetting time is less than 3 seconds. As to the commercial product Leophen FR-M, which is commonly used in the market for textile manufacturing, wetting time is more than 3 seconds. DGM, TGM, HGM and SAS also give very good wettability and their wetting time is also better than commercial product Leophen FR-M. In addition, IPE1312 combined with SAS60 can also provide very good wettability.

TABLE 3

(pH: 7.0)

| Materials | Number | | | | |
|---|---|---|---|---|---|
| | 1 | 2 | 3 | 4 | 5 |
| Pectinase-A | 1.15 mg protein/L | 1.15 mg protein/L | 1.15 mg protein/L | 1.15 mg protein/L | 1.15 mg protein/L |
| Surfactants | IPE1305 1.5 g/L | IPE1306 1.5 g/L | IPE1308 1.5 g/L | IPE1312 1.5 g/L | Leophen FR-M 1.5 g/L |
| Result | | | | | |
| Wetting time, (second) | 2.5 | 2 | 1.2 | 1.7 | 4 |

| Materials | Number | | | | |
|---|---|---|---|---|---|
| | 6 | 7 | 8 | 9 | 10 |
| Pectinase-A | 1.15 mg protein/L | 1.15 mg protein/L | 1.15 mg protein/L | 1.15 mg protein/L | 1.15 mg protein/L |
| Surfactants | DGM 1.5 g/L | TGM 1.5 g/L | HGM 1.5 g/L | SAS 1.5 g/L | IPE1312:SAS (3:1) Total 1.5 g/L |
| Result | | | | | |
| Wetting time, (second) | 1.9 | <1 | 2.1 | <1 | <1 |

Example 3: Bioscouring on Knitted Fabric with Pectinase and Surfactants

Knitted fabrics were cut into 25 cm×25 cm and weighted. Liquor ratio: 10:1

Bioscouring process: as in example 2.

In order to identify the relationship between pectinase and surfactants, we compared the wetting time by using Pectinase-A or surfactants. From Table 4, it can be concluded that when only using Pectinase-A treatment or only surfactant treatment, both wetting time are more than 20 seconds. Therefore, both pectinase and surfactant are necessary for bioscouring process.

TABLE 4

| Materials | Number | | |
|---|---|---|---|
| | 1 | 2 | 3 |
| Pectinase-A | 1.15 mg protein/L | 1.15 mg protein/L | / |
| Surfactants | IPE1312 1.5 g/L | / | IPE1312 1.5 g/L |
| Result | | | |
| Wetting time, second | 1.7 | >180 | 20.5 |

Example 4: Cellulase Boosts Wettability Performance on Knitted Fabric

Knitted fabrics were cut into 25 cm×25 cm and weighted. Liquor ratio: 10:1

Bioscouring process: as in example 2.

TABLE 5

(pH: 7.0)

| Materials | Number | |
|---|---|---|
| | 1 | 2 |
| Pectinase-A | 1.15 mg protein/L | 1.15 mg protien/L |
| Cellulase-C | / | 2 mg protein/L |
| Surfactants | IPE1306 1.0 g/L | IPE1306 1.0 g/L |
| Result | | |
| Wetting time, s | 2.8 | 1.3 |

In this study, we tested the cellulase effect on bioscouring. Above result shows that if adding cellulase in bioscouring process together with pectinase and surfactant, wettability can be improved greatly. Therefore, it is concluded that cellulases have boosting effect on wettability improvement.

Example 5: Bioscouring on Cone Yarn with Pectinase/Cellulase and Surfactants Yarn: 32 s/2 combed Cone yarn. Liquor ratio: 7:1
Bioscouring Process:

0.8 g/L surfactant and 2.54 mg protein/L pectinase and 1.35 mg protein/L cellulase were added to Gofront Cone sample Dyeing machine. The yarns were treated 15 minutes at 55° C., then 80° C. for 10 minutes, and then the yarns were rinsed using cold water and drained. The yarns were then ready for dyeing.

By comparing, a conventional method for yarn scouring was conducted, in which yarns were incubated with 1.5 g/l X-NF and 1.5 g/l FMFD for 30 minutes at 100° C., and then treated with hot rinse and cold rinse. From Table 6, it can be seen that the absorbency (s) after bioscouring with Pectinase-A, Cellulase C and surfactant is better than that after scouring by the conventional process.

TABLE 6

(pH: 7.4-7.6)

| Materials | Method | |
|---|---|---|
| | Conventional process | Bio-scouring process |
| Pectinase-A | / | 2.54 mg protein/L |
| Cellulase-C | / | 1.35 mg protein/L |
| Surfactants | X-NF: 1.5 g/L FMFD: 1.5 g/L | IPE1310 0.8 g/L |
| Result | | |
| Wetting time, (second) | >180 s | 40-60 s |

Example 6: Combined Desizing and Scouring by Using IPE1312 and SAP Process on Woven Fabric Raw woven fabric of 100% cotton: 20×16/128×60, which means the count of warp and weft are 20 and 16, and the density of warp and weft is 128 and 60 (the larger the count corresponds to the higher fabric quality). The raw woven fabric came from Hebei Ningfang Group, China.

Wet pick up (WPU): The wet pick up is a padding solution percentage and usually expressed as a percentage on the weight of the dry untreated fabric.

Process on Woven Fabric:

The raw woven fabric used in this study is 20×16/128×60 and 100% cotton. Firstly, 50 ml padding solution comprising pectinase, amylase, cellulase and surfactants of each swatch was prepared as in Table 7 below and then one piece of woven fabric of around 15 g (25 cm×25 cm) was put into the padding solution beaker and impregnated. The wet pick up (WPU) was 70%. After that, all swatches were stored at room temperature overnight (16-20 hours). About 16 to 20 hours later, all samples were rinsed in five wash baths sequentially. The temperature of the five wash baths was 95° C. After desizing and scouring, all samples were bleached as conventional method except doubling $H_2O_2$ dosage from 5 g/L to 10 g/L. The recipe was described in Table 8. All swatches were put into bleaching solution (WPU:30%) and then steamed for 30 minutes in a steam box. After bleaching, all swatches were rinsed again using four wash bath with the water temperature of 95° C. In order to remove surfactant completely, the swatches were treated by hand wash at 50° C. for 10 times and rinsed in a Wascator (Electrolux, Switzerland) twice. The Wascator rinsing procedure was 50° C., 10 L deionized water for 5 minutes, and followed by 30° C., 10 L deionized water for 5 minutes. Fabric was dried at 105° C. for 30 minutes.

TABLE 7

(pH: 7.0):

| Materials | Number 1 | Number 2 | Number 3 |
|---|---|---|---|
| Pectinase-A | 14.4 mg protein/L | 14.4 mg protein/L | 14.4 mg protein/L |
| Aquazym SD-L | 5 g enzyme product/L | 5 g enzyme product/L | 5 g enzyme product/L |
| Cellulase-C | 20 mg protein/L | 20 mg protein/L | 20 mg protein/L |
| Surfactants | 80% IPE1312 + 20% SAP 4 g/L | 80% OGM + 20% SAP 4 g/L | F-OLB 4 g/L |
| Rinse | | | |
| Bleaching (see table 8) | | | |
| Rinse | | | |
| Dry 105° C. for 30 min | | | |
| Result | | | |
| Wetting time, (second) | <1 | <1 | <1 |
| Wicking, (cm) | 8.3 | 6.7 | 6.8 |
| TEGEWA | 6 | 6 | 5.5 |
| CIE whiteness | 63.14 | 62.04 | 62.39 |

TABLE 8

Bleaching recipe

| Chemicals | Dosage, g/L |
|---|---|
| Peroxide (100%) | 10 |
| Prestogen ® PL | 10 |
| Leophen FR-M | 1 |
| NaOH | 2 |
| Other parameters | |
| pH | About 10.5 |

The study shows that 80% IPE1312 with 20% SAP gives a satisfying wicking value, CIE whiteness, TEGEWA, which meets the mill's expectation. Meanwhile, comparing with Kieralon® Wash F-OLB Conc, the wettability of 80% IPE1312 and 20% SAP is much better.

Example 7: Combined Desizing and Bioscouring

Process: the same as the process in Example 6.

TABLE 9

(pH: 7.0)

| Materials | Number 1 | Number 2 | Number 3 |
|---|---|---|---|
| Pectinase-A | / | 14.4 mg protein/L | 14.4 mg protein/L |
| Aquazym SD-L | 5 g enzyme product/L | 5 g enzyme product/L | 5 g enzyme product/L |
| Cellulase-C | / | / | 33.3 mg protein/L |
| Surfactants | 70% IPE1312 + 30% SAP 5 g/L | 70% IPE1312 + 30% SAP 5 g/L | 70% IPE1312 + 30% SAP 5 g/L |
| Rinse | | | |
| Bleaching | | | |
| Rinse | | | |
| Dry 105° C. for 30 min | | | |
| Result | | | |
| Wetting time, s | 2.5 | <1 | <1 |
| Wicking, cm | 3.7 | 5.95 | 6.95 |
| TEGEWA | 5.5 | 5.5 | 5.5 |
| CIE whiteness | 60.66 | 63.31 | 62.89 |

Above result shows that amylase only gives wicking value of 3.7 cm and wetting time is more than 1 second. If pectinase is added into a pre-treatment solution, wicking value improves significantly. As in the knitted fabric study (Example 4), cellulase could also boost wettability on woven fabric.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A method for scouring a cellulosic textile, comprising treating the cellulosic textile with a pectinase and a surfactant of the formula R—(CH$_2$)$_9$—CH$_2$—(CH$_2$CH$_2$O)$_n$—H, wherein R is —CH—(CH$_3$)$_2$ and 6≤n≤12, and wherein
   the surfactant is added at a concentration of 1 to 10 mM; and
   the pectinase is added in an amount of 0.01 to 1 mg enzyme protein per gram of the textile.
2. The method of claim 1, wherein n is 6.
3. The method of claim 1, wherein n is 8.
4. The method of claim 1, wherein n is 10.
5. The method of claim 1, wherein n is 12.
6. The method of claim 1, wherein the pectinase is a pectate lyase.
7. The method of claim 2, wherein the pectinase is a pectate lyase.
8. The method of claim 3, wherein the pectinase is a pectate lyase.
9. The method of claim 4, wherein the pectinase is a pectate lyase.
10. The method of claim 5, wherein the pectinase is a pectate lyase.
11. The method of claim 6, wherein the amino acid sequence of the pectinase has at least 60% sequence identity with SEQ ID NO: 1.
12. The method of claim 1, which further comprises treating the cellulosic textile with a cellulase.
13. The method of claim 12, wherein the cellulase is an endoglucanase.
14. The method of claim 1, further comprising treating the cellulosic textile with one or more enzymes selected from the group consisting of amylase, catalase, cutinase, lipase, mannanase, oxidase, protease, and xylanase.

* * * * *

SEQUENCE LISTING

```
<160> NUMBER OF SEQ ID NOS: 2

<210> SEQ ID NO 1
<211> LENGTH: 341
<212> TYPE: PRT
<213> ORGANISM: Bacillus licheniformis
<220> FEATURE:
<221> NAME/KEY: SIGNAL
<222> LOCATION: (1)..(27)

<400> SEQUENCE: 1

Met Lys Lys Leu Ile Ser Ile Ile Phe Ile Phe Val Leu Gly Val Val
1               5                   10                  15

Gly Ser Leu Thr Ala Ala Val Ser Ala Glu Ala Ala Ser Ala Leu Asn
                20                  25                  30

Ser Gly Lys Val Asn Pro Leu Ala Asp Phe Ser Leu Lys Gly Phe Ala
        35                  40                  45
```

```
Ala Leu Asn Gly Gly Thr Thr Gly Glu Gly Gly Gln Thr Val Thr
    50                  55                  60

Val Thr Thr Gly Asp Gln Leu Ile Ala Leu Lys Asn Lys Asn Ala
 65              70                  75                  80

Asn Thr Pro Leu Lys Ile Tyr Val Asn Gly Thr Ile Thr Ser Asn
                 85                  90                  95

Thr Ser Ala Ser Lys Ile Asp Val Lys Asp Val Ser Asn Val Ser Ile
                100                 105                 110

Val Gly Ser Gly Thr Lys Gly Glu Leu Lys Gly Ile Gly Ile Lys Ile
                115                 120                 125

Trp Arg Ala Asn Asn Ile Ile Arg Asn Leu Lys Ile His Glu Val
130                 135                 140

Ala Ser Gly Asp Lys Asp Ala Ile Gly Ile Glu Gly Pro Ser Lys Asn
145                 150                 155                 160

Ile Trp Val Asp His Asn Glu Leu Tyr His Ser Leu Asn Val Asp Lys
                    165                 170                 175

Asp Tyr Tyr Asp Gly Leu Phe Asp Val Lys Arg Asp Ala Glu Tyr Ile
                180                 185                 190

Thr Phe Ser Trp Asn Tyr Val His Asp Gly Trp Lys Ser Met Leu Met
        195                 200                 205

Gly Ser Ser Asp Ser Asp Asn Tyr Asn Arg Thr Ile Thr Phe His His
        210                 215                 220

Asn Trp Phe Glu Asn Leu Asn Ser Arg Val Pro Ser Phe Arg Phe Gly
225                 230                 235                 240

Glu Gly His Ile Tyr Asn Asn Tyr Phe Asn Lys Ile Ile Asp Ser Gly
                245                 250                 255

Ile Asn Ser Arg Met Gly Ala Arg Ile Arg Ile Glu Asn Asn Leu Phe
                260                 265                 270

Glu Asn Ala Lys Asp Pro Ile Val Ser Trp Tyr Ser Ser Ser Pro Gly
                275                 280                 285

Tyr Trp His Val Ser Asn Asn Lys Phe Val Asn Ser Arg Gly Ser Met
            290                 295                 300

Pro Thr Thr Ser Thr Thr Thr Tyr Asn Pro Pro Tyr Ser Tyr Ser Leu
305                 310                 315                 320

Asp Asn Val Asp Asn Val Lys Ser Ile Val Lys Gln Asn Ala Gly Val
                325                 330                 335

Gly Lys Ile Asn Pro
            340

<210> SEQ ID NO 2
<211> LENGTH: 299
<212> TYPE: PRT
<213> ORGANISM: Thielavia terrestris
<220> FEATURE:
<221> NAME/KEY: VARIANT
<222> LOCATION: (1)..(299)
<220> FEATURE:
<221> NAME/KEY: SIGNAL
<222> LOCATION: (1)..(21)

<400> SEQUENCE: 2

Met Arg Ser Thr Pro Val Leu Arg Thr Thr Leu Ala Ala Ala Leu Pro
 1               5                  10                  15

Leu Val Ala Ser Ala Ala Ser Gly Ser Gly Gln Ser Thr Arg Tyr Trp
                20                  25                  30

Asp Cys Cys Lys Pro Ser Cys Ala Trp Pro Gly Lys Ala Ala Val Ser
                35                  40                  45
```

-continued

```
Gln Pro Val Tyr Ala Cys Asp Ala Asn Phe Gln Arg Leu Ser Asp Phe
     50                  55                  60
Asn Val Gln Ser Gly Cys Asn Gly Gly Ser Ala Tyr Ser Cys Ala Asp
 65                  70                  75                  80
Gln Thr Pro Trp Ala Val Asn Asp Asn Leu Ala Tyr Gly Phe Ala Ala
             85                  90                  95
Thr Ser Ile Ala Gly Gly Ser Glu Ser Ser Trp Cys Cys Ala Cys Tyr
            100                 105                 110
Ala Leu Thr Phe Thr Ser Gly Pro Val Ala Gly Lys Thr Met Val Val
             115                 120                 125
Gln Ser Thr Ser Thr Gly Gly Asp Leu Gly Ser Asn His Phe Asp Ile
     130                 135                 140
Ala Met Pro Gly Gly Gly Val Gly Ile Phe Asn Gly Cys Ser Ser Gln
145                 150                 155                 160
Phe Gly Gly Leu Pro Gly Ala Gln Tyr Gly Gly Ile Ser Ser Arg Asp
             165                 170                 175
Gln Cys Asp Ser Phe Pro Ala Pro Leu Lys Pro Gly Cys Gln Trp Arg
             180                 185                 190
Phe Asp Trp Phe Gln Asn Ala Asp Asn Pro Thr Phe Thr Phe Gln Gln
             195                 200                 205
Val Gln Cys Pro Ala Glu Ile Val Ala Arg Ser Gly Cys Lys Arg Asn
     210                 215                 220
Asp Asp Ser Ser Phe Pro Val Phe Thr Pro Pro Ser Gly Gly Asn Gly
225                 230                 235                 240
Gly Thr Gly Thr Pro Thr Ser Thr Ala Pro Gly Ser Gly Gln Thr Ser
             245                 250                 255
Pro Gly Gly Gly Ser Gly Cys Thr Ser Gln Lys Trp Ala Gln Cys Gly
             260                 265                 270
Gly Ile Gly Phe Ser Gly Cys Thr Thr Cys Val Ser Gly Thr Thr Cys
             275                 280                 285
Gln Lys Leu Asn Asp Tyr Tyr Ser Gln Cys Leu
     290                 295
```